United States Patent
Franke

(10) Patent No.: US 7,879,357 B2
(45) Date of Patent: Feb. 1, 2011

(54) PHARMACEUTICAL COMPOSITION IN THE FORM OF A HYDROGEL FOR TRANSDERMAL ADMINISTRATION OF ACTIVE INGREDIENTS

(75) Inventor: Patrick Franke, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 1188 days.

(21) Appl. No.: 10/833,273

(22) Filed: Apr. 28, 2004

(65) Prior Publication Data

US 2005/0003009 A1    Jan. 6, 2005

Related U.S. Application Data

(60) Provisional application No. 60/465,808, filed on Apr. 28, 2003.

(30) Foreign Application Priority Data

Apr. 28, 2003 (EP) .................................. 03008856

(51) Int. Cl.
- *A61K 9/14* (2006.01)
- *A61K 31/40* (2006.01)
- *A61K 31/265* (2006.01)

(52) U.S. Cl. ......................... 424/486; 514/408; 514/512

(58) Field of Classification Search ................. 424/486; 514/277, 408, 512
See application file for complete search history.

(56) References Cited

U.S. PATENT DOCUMENTS

| | | | |
|---|---|---|---|
| 5,460,620 A | * | 10/1995 | Smith et al. .................. 604/290 |
| 5,968,547 A | * | 10/1999 | Reder et al. .................. 424/449 |
| 6,267,984 B1 | | 7/2001 | Beste et al. |
| 6,416,742 B1 | | 7/2002 | Stefely et al. |
| 6,503,894 B1 | | 1/2003 | Dudley et al. |

FOREIGN PATENT DOCUMENTS

| | | | |
|---|---|---|---|
| EP | 0573133 | | 12/1993 |
| EP | 0811381 | | 12/1997 |
| FR | 2518879 | | 7/1983 |
| WO | WO 8809185 | | 12/1988 |
| WO | WO 93/25168 | * | 12/1993 |
| WO | WO 9325168 | | 12/1993 |
| WO | WO 99/13812 | * | 1/1999 |
| WO | WO 99/13812 | * | 3/1999 |

OTHER PUBLICATIONS

Suvisaari et al., "Pharmacokinetics of 7α-methyl-19-nortestosterone (MENT™) delivery using subdermal implants in healthy men," in Contraceptioon, vol. 60, Issue 5, Nov. 1999, pp. 299-303.*
Peppas N A et al: "Hydrogels in pharmaceutical formulations," European Journal of Pharmaceutics and Biopharmaceutics, Jul. 3, 2000, pp. 27-46, vol. 50, No. 1, XP004257178, ISSN: 0939-6411, the entire document, Elsevier Science Publishers B.V., Amsterdam, NL.

* cited by examiner

*Primary Examiner*—Blessing M Fubara
(74) *Attorney, Agent, or Firm*—Millen, White, Zelano, Branigan, P.C.

(57) ABSTRACT

The invention relates to a pharmaceutical composition in the form of a hydrogel that comprises a carboxylic acid diester, a $C_2$-$C_4$ alkyl alcohol, an active ingredient and a polymer matrix. The invention also relates to the use of a carboxylic acid diester as a transdermal permation enhancer for an active ingredient in a pharmaceutical composition in the form of a hydrogel, whereby the composition comprises a polymer matrix and a $C_2$-$C_4$ alkyl alcohol. The invention also relates to a sweat-resistant composition in the form of a hydrogel, which comprises an acrylic polymer in combination with a cellulose derivative.

5 Claims, 2 Drawing Sheets

Permeation of eF-MENT (0.8%) Through Mouse Skin from Transdermal Gels

PHARMACEUTICAL COMPOSITION IN THE FORM OF A HYDROGEL FOR TRANSDERMAL ADMINISTRATION OF ACTIVE INGREDIENTS

This application claims the benefit of the filing date of U.S. Provisional Application Ser. No. 60/465,808 filed Apr. 28, 2003.

The invention relates to a pharmaceutical composition in the form of a hydrogel, with whose help active ingredients (pharmaceutical substances), especially steroid hormones and their derivatives, can be administered transdermally. In a preferred embodiment, the hydrogel contains propylene carbonate, ethanol and 7α-methyl-11β-fluoro-19-nortestosterone (eF-MENT). The invention also relates to a pharmaceutical composition in the form of a hydrogel, which has special physical properties, especially increased bonding strength, and can therefore be applied especially well to the skin.

The systemic administration of steroid hormones can be carried out in principle with an oral method with the aid of suitable dosage forms. The bioavailability in oral administration is frequently reduced, however, since the active ingredients are metabolized in the liver before they pass into the systemic blood circulation (so-called "first-pass metabolism"). Also, special requirements are generally set on the dosage forms in the case of oral administration, since the release of steroid hormones should be carried out as uniformly as possible over an extended period. To avoid the oral administration of steroid hormones, certain steroid derivatives were developed that are suitable in particular for injection. In this respect, reference can be made to, for example, the publications WO 99/67270 and WO 99/67271. Another possibility, to administer the steroid hormones continuously and bypassing the first-pass effect, consists in the use of suitable implants. Implants for administering androgens and their derivatives are disclosed in, for example, the following publications: EP-A 970 704, WO 97/30656, WO 99/13883, WO 00/28967, U.S. Pat. No. 5,733,565, K. Sundaram et al., *Annuals of Medicine,* 1993, 25 (2), 199; R. A. Anderson et al., *J. Clin. Endocrin. & Metab.,* 1999, 84(10) 3556 and J. Suvisaari et al., *Contraception,* 1999, 60(5), 299. These implants have the drawback, however, that they must be inserted in patients by an operative intervention by a physician and must be removed again. Such operative interventions always entail a certain risk of infection. Also, there exists in the population a basic aversion to such dispensing methods, especially if alternative processes for systemic administration are available.

To avoid the pharmacological drawbacks of oral administration, on the one hand, and the drawbacks of invasive, purely mechanical penetration of the skin with the aid of medical instruments (hypodermic needles, scalpels), on the other hand, processes were developed with whose aid the active ingredient continuously diffuses through the skin over a specific time span and thus enters the systemic blood circulation.

The skin represents the largest organ of the human body with a surface area of approximately 20,000 cm$^2$ and receives approximately one third of the entire blood supply in the organism (cf. Y. W. Chien, *Logics of Transdermal Controlled Drug Administration. Drug Dev. Ind. Pharm.* 1983, 9, 497). It primarily exerts protective functions: it prevents the penetration of foreign substances and microorganisms and the loss of essential endogenic substances such as water and electrolytes. The skin, however, does not form any fully impermeable barriers for exogenic substances, such that active ingredients can be taken up transcutaneously in the organism via different methods. The percutaneous permeability is decisively influenced by the site of administration and by the thickness of the horny layer, which represents the main barrier for foreign substances. While hydrocortisone is taken up as a model substance on hand surfaces and the soles of the feet to a lesser extent, the uptake rate through the skin of the retro-auricular region and the scrotum is increased up to 40× compared to the lower arm (cf. H. Asche, *Konzept und Aufbau transdermaler therapeutischer Systeme [Concept and Design of Transdermal Therapeutic Systems]. Schweiz [Switzerland]. Rundsch. Med. Prax.,* 1985, 74, 3).

An active ingredient can thus act transdermally, but it must diffuse through the epidermis of the skin in an adequate amount and be taken from the blood circulation. In this case, the epidermis exerts an intensive barrier function, which can be attributed, on the one hand, to the fact that the relevant active ingredient must pass in succession through hydrophilic and lipophilic layers and then again hydrophilic layers, but, on the other hand, the low water content in the stratum corneum also hampers the diffusion of active ingredients. The permeation of the horny layer that is necessary for a systemic action and also for the action of the active ingredients to be administered externally in most cases is carried out in the undamaged skin in a transepidermal manner (in an intercellular or transcellular manner) and through pores (in a transglandular or transfollicular manner) (cf. K. Karzel et al., *Mechanismen transkutaner Resorption—Pharmakologische und biochemische Aspekte [Mechanisms of Transcutaneous Resorption—Pharmacological and Biochemical Aspects]. Arzneim.-Forsch. Drug Res.* 1989, 39, 1487).

Conceptually, the penetration of an active ingredient can be distinguished from the permeation of an active ingredient: penetration means that the active ingredient gets into the skin, while in the case of permeation, the active ingredient goes through the skin into the blood stream. For systemic administration of active ingredients via the blood circulation, a permeation is therefore necessary.

For transdermal administration, active ingredient-containing patches were developed with whose aid the active ingredients can pass into the systemic blood circulation. By diffusion, the active ingredient passes into the tissue that lies beneath the skin and is released to the blood vessels, such that it can exert its effectiveness systemically.

Active ingredient-containing patches have the drawback, however, that they are applied noticeably and visibly to the skin for the period of the administration of the active ingredient. Also, the cover film of the patch provides occlusion conditions. The swelling of the skin that is produced in this respect can result in altered diffusion conditions for the active ingredient. The active ingredient is incompletely released to the skin in most patch types. The removal of the patch occasionally causes the patient pain, since the body hair adheres to the adhesive surfaces of the patch and thus hair is torn out by the roots when the patch is removed. Also, transdermal patches have the drawback that the contact adhesive that is used in the patients frequently produces allergies and skin irritations. Also, the repeated sticking and tearing-off of the active ingredient-containing patch with repeated use on the same skin parts can result in skin reddening and irritation over time.

An essential drawback of active ingredient-containing patches also consists in the fact that they are limited in their contact surface area on the skin. Since, however, comparatively high plasma concentrations are necessary for the effectiveness of many active ingredients, the latter, however, can be achieved only with large-area administration of the active ingredient through the skin; active ingredient-containing patches quickly reach their limits. This is especially the case when a specific active ingredient shows an unfavorable permeation behavior, which can be compensated only by a corresponding large-area skin contact. In general, the assumption can be made that patches with a size of more than 50 cm² are only conditionally suitable for use. Since, in active ingredient-containing patches, the surface area of the system is limited, only highly potent active ingredients can be used, whose active plasma levels lie in the range of ng/ml. Relative to other units, for example, reference can be made to K. H. Bauer et al, *Lehrbuch der pharmazeutischen Technologie [Textbook for Pharmaceutical Technology], Wissenschaftliche Verlagsgesellschaft mbH Stuttgart,* 1999, 6th Edition.

As an alternative to the active ingredient-containing patches, active ingredient-containing gels were developed that are applied to the skin and dry on the skin surface within a short time. The drying is carried out, on the one hand, by evaporating the solvent, depending on the type of solvent that is used, but it is also possible that at least a certain portion of the solvent penetrates selectively from the gel in the skin directly after the gel is applied.

Active ingredient-containing gels, which contain a polymer matrix, are distinguished in that after the drying on the skin, a thin film that consists of the polymer matrix remains, in which the active ingredient and the other non-volatile components of the gel are embedded. In the dry state, the polymer matrix controls the diffusion of the active ingredient through the skin and thus makes possible a controlled release to the organism over an extended time span. Such a controlled, time-monitored and continuous release of the active ingredient to the blood circulation is desirable especially in hormones and hormone derivatives, such that these active ingredient-containing gels are especially suitable for administering such active ingredients. By bypassing the gastrointestinal tract in the case of transdermal administration, the disadvantageous first-pass metabolism is also avoided. The dosage of the active ingredient can be easily controlled by varying the amount of gel and the surface area on which the gel is applied. The duration of action of active ingredients with short biological half-lives can be extended in this way. In the case of active ingredients with a narrow therapeutic range of action, side effects diminish, and patient compliance is also frequently better.

Active ingredient-containing gels represent true one-phase systems. These are semisolid systems in which liquids are solidified by gel skeleton formers. Hydrogels and oleo gels are differentiated depending on whether the liquid that forms the gel is water or an oil. The hydrogels consist of an aqueous active ingredient solution that is solidified into a gel primarily with macromolecular hydrophilic substances. As gel skeleton formers, organic polymers, but also inorganic substances, such as, e.g., bentonite and highly disperse silicon dioxide, can be used. Oleo gels are oils that had been stiffened with gel skeleton formers.

Hydrogels are distinguished from ointments, i.a., in that ointments are preparations that do not contain any aqueous phase. Hydrogels are distinguished from creams in that they do not contain any lipid phase. Relative to further details for limiting the hydrogels of other semi-solid dosage forms, reference can be made to, for example, K. H. Bauer et al, *Lehrbuch der pharmazeutischen Technologie, Wissenschaftliche Verlagsgesellschaft mbH Stuttgart,* 1999, 6th Edition.

Relative to active ingredient-containing patches, gels have the advantage that after drying on the skin, only a thin film from the components of the gel remains, which cannot immediately evaporate or penetrate the skin. By drying, a very close contact between the outside skin layer and the gel residue is produced, and pores and extremely small bumps on the skin are reached by the fluid gel, which can be achieved only with difficulty with active ingredient-containing patches. Stretching of the skin, which is caused by movements of the patient, is not a problem because of the elasticity and the adhesion of the gel residue over the entire contact surface. However, such stretching of the skin in the case of active ingredient-containing patches frequently results in an undesirable lateral movement of the contact surface of the patch and the outer skin layer. The patient does not feel the active ingredient being taken up, and his physical movements are also otherwise unimpaired. The gels can also be applied on a large area of the skin, such that active ingredients, which are unsuitable for active ingredient-containing patches, can also be administered transdermally. This is an essential advantage of the gels compared to the patches. After the release of active ingredients is completed, the thin film residue, which remains on the skin, can be washed off with water. Skin irritations are generally less than with transdermal patches, nevertheless they produce a problem with many hydrogels, especially since these gels have considerable amounts (about 70% in hydrogels used at this time) of ethanol to improve the permeation. The high ethanol content is necessary to ensure good permeation but results in skin irritations.

In addition to the compatibility and the good permeation, specific physical requirements are also set on active ingredient-containing gels. Their consistencies must be constituted such that they can be easily applied to the skin and have enough gel strength that the gel skeleton is maintained, while the volatile components evaporate or are drawn into the skin. The amount of gel that must be applied to the skin per dosage unit is usually 1-5 ml. In the prior art are known polyacrylic acid-based gels that upon skin contact experience an immediate partial liquefaction. The reason for this is the deficient electrolyte tolerance of these gel systems. Owing to salts in the hydrolipid film on the skin, this effect causes the products to quickly run off or drip off. Special problems also arise if the skin surface contains large concentrations of salt and is moist because of perspiration. The application behavior that is problematical in nature is especially disadvantageous against the backdrop that in the administration of highly potent steroid hormones, a specific use is necessary at its destination. In addition to the effectiveness, in this connection safety (risk of contamination) also plays a role.

Compared to the polyacrylic acid-based gels, the use of cellulose derivatives as hydrogel formers that is also known in the prior art has the drawback of deficient sensory properties as well as larger amounts of residues of the gel former on the skin. The concentrations needed to form a gel skeleton are 2-3× higher compared to polyacrylates and produce a so-called "eraser effect" (rippling) after application on the skin. These residues are also undesirable for appropriate use of a hydrogel for transdermal administration of active ingredients.

U.S. Pat. No. 6,010,716 discloses a pharmaceutical composition for transdermal administration that comprises a polymer matrix that forms a flexible film after drying. The polymer matrix is selected from cellulose polymers or cellulose copolymers or vinyl pyrrolidone/vinyl acetate copolymers.

Various requirements are linked to the physical and chemical properties of active ingredients that are suitable for a transdermal therapy with the aid of gels. The molecular weight should be less than 1000 $gmol^{-1}$. The substance should be lipid-soluble, but also exhibit a certain solubility in aqueous media. As active ingredients that are suitable in principle for transdermal administration because of their physical and chemical properties, steroids are especially advantageous from the pharmacological standpoint. In this case, these are in particular steroids with androgenic action (androgens).

In many cases, the addition of a permeation enhancer is necessary for achieving the plasma concentration that is adequate for the action. Many permeation enhancers were examined for this purpose, and reference can be made to, for example, E. W. Smith et al., *Percutaneous Penetration Enhancers*, CRC Press, 1995.

Various compositions for transdermal administration of steroid hormones, i.a., certain androgens (especially testosterone), are known in the prior art and are disclosed in, for example, WO 96/08255, WO 97/03698, WO 97/43989, WO 98/37871, WO 99/13812, WO 00/71133, WO 02/066018 and A. W. Meikle et al, *J. Clin. Endocrin. & Metab.* 1992, 74, 623. A common feature of the compositions for transdermal administration that are described in the publications above is that the steroid hormone in combination with at least one permeation enhancer is administered only to ensure that the active ingredient permeates through the skin at all. As examples of known permeation enhancers that are described for testosterone, fatty acids, fatty acid esters with simple alcohols, fatty acid monoesters with multivalent alcohols, fatty alcohols and terpenes can be mentioned. There is an essential difference between active ingredient-containing patches and active-ingredient-containing gels, such that it cannot be concluded that a permeation enhancer that is suitable for an active ingredient-containing patch is also suitable for an active ingredient-containing gel. This is thus associated with the fact that, i.a., active ingredient-containing gels dry after application on the skin, while in active ingredient-containing patches, a back layer that is impermeable to the solvent normally prevents a drying-out.

Active ingredient-containing patches sometimes contain in their interior a gelled core in which the active ingredient and some adjuvants are embedded. In this connection, reference can be made to, for example, publication EP-A 208 395. Such gelled cores of active ingredient-containing patches cannot be compared with active ingredient-containing gels, which in this respect are intended to be applied to the skin, in their properties for the above-mentioned reasons, however.

Currently, in practice only those active ingredient-containing gels that contain large amounts of ethanol (70% by weight and more) are used since it is assumed that with smaller amounts of ethanol, the necessary permeation rates cannot be reached. Gels with lower ethanol contents are described but are not used in practice because of their low permeation rates. The problems associated with the high ethanol content, such as reddening, swelling and permanent damage and tears in the skin are tolerated. In the prior art, a start is made from the fact that low-molecular alkyl alcohols, such as, e.g., ethanol, increase the fluidity of the liquids in the stratum corneum or extract lipids from the stratum corneum and thus enhance the permeation of the active ingredient through the skin.

EP-A 811 381 discloses a gel that contains an estrogen and/or a progestin, a linear aliphatic primary alcohol with 11-19 carbon atoms, a monoalkyl ether of diethylene glycol, an alcohol with 2-4 carbon atoms, glycol, water, a polymer or copolymer that consists of acrylic acid and a tertiary amine. Such gels have in particular, however, the drawback that the permeation properties for many active ingredients are not completely satisfactory. The permeation properties of these formulations can be improved by the water content being reduced and the content of alcohol being increased, but this does not necessarily lead to a reduced compatibility.

A problem that also occurs when using transdermal gels consists of the fact that pharmaceutical compositions in the form of hydrogels often run off after application on the skin, by which the gel skeleton that is necessary for the controlled release of the active ingredient is destroyed and possible dripping-off of the product both reduces patient compliance and increases the probability of contamination of inappropriate areas or objects. This problem occurs in normal skin conditions. It occurs to an especially large extent if the hydrogels are applied to "sweaty" skin, such that with known and commercially available gels, it is required that the skin be basically cleaned before the gel is applied. A hydrogel should preferably also remain intact, however, if it is applied to skin that is not completely sweat-free.

Treatment with transdermal gels is frequently a long-term therapy, especially in the case of the administration of steroids. For the success of such treatments, in addition to the effective administration of the active ingredient (a high permeation rate), patient compliance is decisive. If a patient breaks off the treatment or does not perform it regularly, since the administration of the gel is considered too expensive (e.g., since the skin must be especially cleaned or clothing can be soiled) or since incompatibility occurs, the entire success of treatment is called into question.

For a treatment with transdermal gels, in addition to a high permeation rate, as linear a permeation as possible is advantageous to maintain as constant an active ingredient level in the blood as possible.

There is thus a need for pharmaceutical compositions that are suitable for transdermal administration of active ingredients and exhibit advantages compared to the compositions of the prior art, especially hydrogels for transdermal administration of active ingredients (so-called "transdermal gels") that associate an excellent compatibility with very good permeation properties.

According to the invention, a hydrogel is available as it is defined in the claims and that combines excellent compatibility with outstanding permeability. In a preferred embodiment, the hydrogel can also be applied to the skin with a pronounced hydrolipid film, without rapid running-off and dripping-off of the hydrogel resulting.

It was found, surprisingly enough, that with the aid of a pharmaceutical composition in the form of a hydrogel, which contains a carboxylic acid diester, a $C_2$-$C_4$ alkyl alcohol, an active ingredient and a polymer matrix, skin irritations and other side effects can be effectively reduced. At the same time, very good results relative to the permeation behavior of different active ingredients are achieved with these compositions.

Pharmaceutical compositions that contain carboxylic acid diesters, especially propylene carbonate, are known in the prior art.

WO 98/10742 discloses a single-phase, anhydrous preparation for topical use, which contains propylene carbonate, at least one alcohol, glycol, glycerol and a therapeutically or cosmetically effective component. The composition is completely anhydrous, and the active ingredients can quickly penetrate the skin. A permeation is not provided, however.

WO 00/41702 discloses a preparation for external use, which contains a 21-alkoxy steroid, propylene carbonate and polyoxyethylene/hardened castor oil. The composition is suitable for topical administration of steroids for the purpose of treating skin diseases, such as, e.g., chronic or acute eczema, atopic dermatitis, contact dermatitis and psoriasis.

JP 590 70 612 discloses a gelled ointment base, which contains a carboxyvinyl polymer, propylene carbonate, propylene glycol, polyethylene glycol and ethanol. The ointment base can contain isopropyl adipate to enhance the penetration of the active ingredient in the skin. Also here, no permeation is to take place.

JP 91 94 396 discloses a composition that comprises an antihistamine, a polymer based on an aminoacrylate, an acid-soluble polymer and a short-chain ester or ether with a total of 4-20 carbon atoms, such as, e.g., isopropyl myristate, triacetin-ethyleneglycol-mononormalbutyl ether or propylene carbonate. The composition can be used as a matrix for a patch.

U.S. Pat. No. 3,924,004 discloses a composition for topical use, which contains a saturated fatty alcohol with 16-24 carbon atoms, propylene carbonate, glycol, a surfactant, a plasticizer, and water. The composition can be used for topical administration of all types of active ingredients, especially anti-inflammatory corticosteroids. The stability of the composition is improved if the composition contains no water.

EP-A 319 555 discloses a transdermal pharmaceutical preparation that has a therapeutic effect and that can be applied as a spray on the skin. The preparation contains a polymer liquid matrix that hardens into a flexible film, an active ingredient, a solvent that controls the release of the active ingredient, in which the active ingredient is at least partially soluble and a solvent for the matrix that evaporates on the skin. As the solvent that controls the release of the active ingredient, sorbitan macrogol laurate and/or paraffin and/or mid-chain fatty acid diglycerides and/or triglycerides and/or propylene carbonate are disclosed. The preparation is anhydrous.

None of these publications discloses a pharmaceutical composition in the form of a hydrogel, which contains a carboxylic acid diester, a $C_2$-$C_4$ alkyl alcohol, an active ingredient and a polymer matrix. The use of carboxylic acid diesters (e.g., of propylene carbonate) as permeation enhancers for active ingredients in pharmaceutical compositions in the form of hydrogels, which contain a polymer matrix and a $C_2$-$C_4$ alkyl alcohol, is also not described in the prior art.

It was found, surprisingly enough, that when using a carboxylic acid diester as a permeation enhancer for the active ingredient, the content of the $C_2$-$C_4$ alkyl alcohol in the composition can be kept relatively low, without in this case having negative effects on the permeation behavior. Special importance is given to the carboxylic acid diester within the composition, since immediately after the pharmaceutical composition is applied, the water and the $C_2$-$C_4$ alkyl alcohol largely evaporate and are drawn into the skin, while the less volatile carboxylic acid diester remains together with the active ingredient in the polymer matrix and thus decisively influences the pharmacokinetic behavior of the active ingredient.

It was found that carboxylic acid diesters are especially compatible and chemically stable, normally do not cause any allergic reactions and interact well with the additional contents that are contained in the pharmaceutical composition, in particular with the water and the $C_2$-$C_4$ alkyl alcohol that are contained in the hydrogel. The proportion by weight of the carboxylic acid diester, the water contained in the composition and the $C_2$-$C_4$ alkyl alcohol can be selected such that the amount of the $C_2$-$C_4$ alkyl alcohol and the side effects caused by the latter are minimized, but simultaneously, nevertheless, very good permeation efficiency for the active ingredient is achieved.

The carboxylic acid diester according to the invention is a chiral compound, such that the latter is preferably in racemic form. It is also possible, however, that the composition according to the invention contains the carboxylic acid diester in concentrated form of an enantiomer or diastereomer.

The carboxylic acid diester preferably exhibits a molecular weight of less than 750 gmol$^{-1}$, more preferably less than 500 gmol$^{-1}$, and especially less than 250 gmol$^{-1}$. The carboxylic acid diester preferably contains no more than 12, but preferably no more than 10, and preferably no more than 7, especially no more than 5, carbon atoms.

In a preferred embodiment according to the invention, the carboxylic acid diester is a compound of general formula (I)

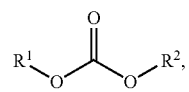

(I)

in which either $R^1$ and $R^2$, independently of one another, are $C_1$-$C_6$-alkyl, $C_2$-$C_6$-alkenyl, $C_2$-$C_6$-alkinyl, $C_4$-$C_6$-cycloalkyl, $C_1$-$C_6$-heterocycloalkyl, phenyl, $C_1$-$C_6$-heteroaryl, phenyl-$C_{1-C4}$-alkyl or $C_2$-$C_{10}$-heteroarylalkyl, whereby the alkyl-, alkenyl- and alkinyl groups optionally can be interrupted in each case up to three times by oxygen atoms and/or sulfur atoms, or $R^1$ and $R^2$,independently of one another, have one of the above-mentioned meanings and are connected to one another via a C—C bond. If $R^1$ and $R^2$ are connected to one another via a C—C bond, the compound of general formula (I) is a cyclic carboxylic acid diester. The $C_1$-$C_6$-heterocycloalkyl-, $C_1$-$C_6$-heteroaryl- and $C_2$-$C_{10}$-heteroarylalkyl groups can contain in the heterocyclic compound 1 to 4 heteroatoms, which are selected independently of one another from N, O and S.

Preferred radicals $R^1$ and $R^2$ (in which the alkyl groups optionally are interrupted up to three times by oxygen atoms and/or sulfur atoms) are presented below:

| | |
|---|---|
| $C_1$—$C_6$-Alkyl: | —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)CH_3$, —$C(CH_3)_3$, —$CH_2OCH_3$, —$CH_2SCH_3$, —$CH_2CH_2OCH_3$, —$CH_2CH_2SCH_3$, —$CH_2CH_2OCH_2CH_3$, —$CH_2CH_2SCH_2CH_3$ and —$CH_2CH_2OCH_2CH_2OCH_2CH_3$; |
| $C_2$—$C_6$-Alkenyl: | —CH=$CH_2$, —$CH_2$CH=$CH_2$, —$CH_2$CH=CH$CH_3$, —CH($CH_3$)CH=$CH_2$, and —CH=C($CH_3$)$_2$; |
| $C_2$—$C_6$-Alkinyl: | —C≡CH, —$CH_2$C≡CH and —$CH_2$C≡C$CH_3$; |
| $C_4$—$C_6$-Cycloalkyl: | -Cyclopentyl and -cyclohexyl; |
| $C_1$—$C_6$-Heterocycloalkyl: | -Piperidyl, -morpholinyl, -tetrahydropyranyl and furanyl; |
| $C_1$—$C_6$-Heteroaryl: | -Pyridyl, -pyrrolyl and -imidazolyl; |
| Phenyl-$C_1$—$C_4$-alkyl: | —$CH_2$-phenyl, —$CH_2CH_2$-phenyl, —$CH_2CH_2$O-phenyl, —$CH_2CH_2$OC$H_2$-phenyl and —$CH_2CH_2$OC$H_2CH_2$O-phenyl; |

-continued

| $C_2$—$C_{10}$-Heteroarylalkyl: | —$CH_2$-Pyridyl, —$CH_2CH_2$-pyridyl, —$CH_2CH_2OCH_2$-pyridyl, —$CH_2CH_2$-imidazolyl, —$CH_2CH_2O$-imidazolyl and —$CH_2CH_2OCH_2$-imidazolyl. |
|---|---|

As preferred radicals $R^1$ and $R^2$, which are connected to one another via a C—C bond, the following bivalent groups can be mentioned:
—$CH_2CH_2$—, —CH═CH—, —$CH(CH_3)CH_2$—, —CH($OCH_3$)$CH_2$—, —$CH(OCH_2CH_3)CH_2$—, —$CH(CH_3)$ $CH(CH_3)$—, —$CH(OCH_3)CH(OCH_3)$—, —$CH_2CH_2CH_2$—, —$CH(CH_3)CH_2CH_2$—, —$CH_2CH(CH_3)CH_2$—, —$CH(CH_3)CH_2CH(CH_3)$— and —$CH_2CH_2OCH_2CH_2$—.

As a permeation enhancer, it is especially preferred that the carboxylic acid diester be a compound of general formula (II)

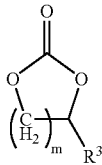

(II)

in which index m is a number from 1 to 3, and $R^3$ is hydrogen or $C_1$-$C_4$-alkyl.

According to the invention, a carboxylic acid diester of general formula (II), in which index m is 1 and $R^3$ is either methyl (propylene carbonate) or hydrogen (ethylene carbonate), is especially preferred.

Propylene carbonate [(±)-4-methyl-1,3-dioxolan-2-one] has a molecular weight of 102 gmol$^{-1}$ and a boiling point of 242° C. It occurs in two enantiomeric forms. In principle, the composition according to the invention can contain propylene carbonate in the pure form of the R-enantiomer or the S-enantiomer or one of the two enantiomers in concentrated form. According to the invention, it is preferred that propylene carbonate be contained in the composition as a racemate.

The proportion by weight of the carboxylic acid diester to the pharmaceutical composition is preferably 1.0-40.0% by weight, more preferably 2.5-3.0% by weight, even more preferably 5.0-20.0% by weight, and especially 7.5-12.5% by weight.

Carboxylic acid diesters are known in the prior art. They can be obtained by, for example, the reaction of alcohols with phosgene or phosgene derivatives. Propylene carbonate can technically be obtained, for example, by reaction of 1,2-propyleneglycol with phosgene. Numerous carboxylic acid diesters are commercially available.

According to the invention, the composition preferably contains a $C_2$-$C_4$ alkyl alcohol that is selected from the group that consists of ethanol, n-propanol and iso-propanol. Ethanol is especially preferred.

The proportion by weight of the $C_2$-$C_4$ alkyl alcohol to the pharmaceutical composition is preferably 25.0-70.0% by weight, more preferably 30.0-65.0% by weight, even more preferably 30.0-60.0% by weight, and especially 40.0-60.0% by weight.

In a preferred embodiment, the relative ratio by weight between the carboxylic acid diester and the $C_2$-$C_4$ alkyl alcohol is 0.01-1.50, preferably 0.08-0.80, especially 0.10-0.30.

In an especially preferred embodiment, the composition according to the invention contains ethanol in combination with ethylene carbonate or propylene carbonate, whereby the combination of ethanol with propylene carbonate is preferred.

The composition according to the invention is suitable in principle for transdermal administration of a wide variety of active ingredients; the composition preferably contains steroids as active ingredients.

In a preferred embodiment, the composition according to the invention contains as active ingredient a compound of general formula (III)

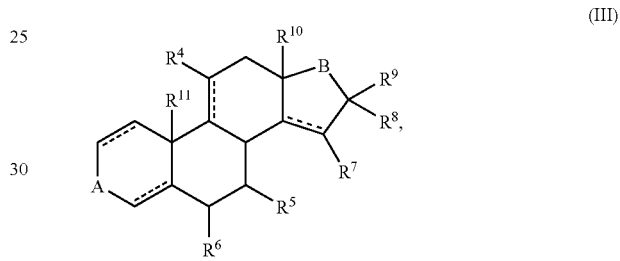

(III)

in which
 $R^4$ is hydrogen, fluorine, chlorine, $C_1$-$C_3$-alkyl or an optionally acetylated hydroxyl group,
 $R^5$, $R^6$, $R^7$, $R^8$, $R^9$, $R^{10}$ and $R^{11}$, independently of one another, are hydrogen or $C_1$-$C_3$-alkyl,
 the dotted lines, independently of one another, are an optional bond, and
 A and B, independently of one another, are a carbonyl group or a group

in which X is a hydroxyl group or its esters of a carboxylic acid with 1-8 carbon atoms, and Y is hydrogen or $C_1$-$C_3$-alkyl. According to the invention, compounds of general formula (III), in which $R^7$, $R^8$ and $R^9$ are hydrogen, are preferred. Compounds of general formula (III) are known in the prior art. Reference can be made to, for example, the publications DE 1 182 229, U.S. Pat. No. 3,341,557, U.S. Pat. No. 4,000, 273, WO 99/26962, WO 02/48169, Hill et al., *Dictionary of Steroids, Chapman and Hall*, 1991, Fieser & Fieser, Steroide [*Steroids*], V C H Weinheim, 1961, J. F. Griffin et al., *Atlas of Steroid Structure*, Plenum Pub Corp, 1984 and G. W. A. Milne, *Ashgate Handbook of Endocrine Agents and Steroids*, Ashgate Publishing Company, 2000.

In an especially preferred embodiment, the composition according to the invention contains as active ingredient a compound of general formula (IV)

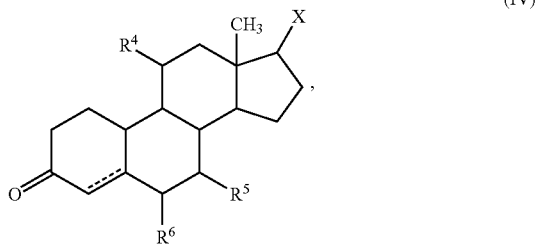

in which X is a hydroxyl group or its esters of a carboxylic acid with 1-4 carbon atoms, $R^4$ is hydrogen, fluorine or a hydroxyl group, $R^5$ and $R^6$, independently of one another, are hydrogen, methyl or ethyl, and the dotted line is an optional bond. The compounds of general formula (IV) are 19-norandrogen derivatives, i.e., the methyl group that is usually contained at carbon atom 19 is replaced by hydrogen. These steroids are often distinguished by a special pharmacological effectiveness.

The compounds of general formula (III) or (IV) can be present in pure form or as a mixture of several stereoisomers. The compounds of general formula (III) or (IV) are preferably present in the form of essentially pure stereoisomers, i.e., the ee or de values are preferably above 90%, more preferably above 95% and especially above 99%.

According to the invention, it is especially preferred if the composition contains as active ingredient a compound of general formula (V)

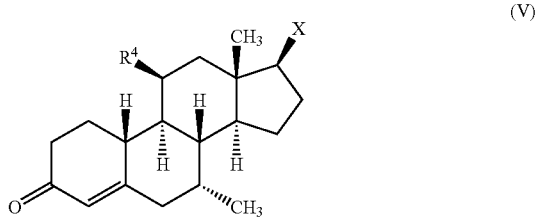

in which $R^4$ is fluorine or hydrogen, and X is a hydroxyl group or its acetate. X is especially preferably a hydroxyl group.

If $R^4$ is hydrogen and X is a hydroxyl group, the compound is 7α-methyl-19-nortestosterone (MENT). If $R^4$ is hydrogen, and radical X of the acetate is a hydroxyl group, the compound is the corresponding acetate (MENTAc). If $R^4$ is fluorine and X is a hydroxyl group, the compound is 7α-methyl-11β-fluoro-19-nortestosterone (eF-MENT). If $R^4$ is fluorine and radical X of the acetate is a hydroxyl group, the compound is the corresponding acetate (eF-MENTAc).

These compounds are known in the prior art; reference can be made to Sundaram et al., Annals in Medicine, 1993, 25, 199 and to WO 2002/59139 A1.

The proportion by weight of the compound of general formula (III), (IV) or (V) to the pharmaceutical composition is 0.001-10.0% by weight, more preferably 0.01-5.0% by weight, even more preferably 0.1-2.5% by weight, and especially 0.5-1.0% by weight.

The relative ratio by weight of the compounds of general formula (III), (IV) or (V) to the carboxylic acid diester is preferably 0.0001-10, more preferably 0.005-1, and especially 0.05-0.1.

In an especially preferred embodiment of the invention, the pharmaceutical composition contains as active ingredient a compound of general formula (V), as $C_2$-$C_4$ alkyl alcohol, ethanol, and as carboxylic acid diester, ethylene carbonate or propylene carbonate, whereby the combination of eF-MENT with ethanol and propylene carbonate is especially preferred.

In a preferred embodiment, the composition according to the invention contains as active ingredient a combination that consists of two or more compounds of general formula (III), (IV) or (V).

It is also possible that the composition according to the invention contains as active ingredient one or more active ingredients that are different from the compounds of formula (III), (IV) or (V). As examples of such active ingredients, androgens, antiandrogens, 5α-reductase inhibitors, estrogen receptor modulators, estrogens, antiestrogens, gestagens, antigestagens, uterus-active substance, m-cholinoceptor antagonists, prostaglandins or prostaglandin derivatives and/or nicotine can be mentioned.

In a preferred embodiment, the composition according to the invention contains a combination that consists of one or more active ingredients of general formula (III), (IV) or (V) and one or more active ingredients that are different from the compounds of formula (III), (IV) or (V). As examples of such active ingredients that are different from the compounds of formula (III), (IV) or (V), androgens, antiandrogens, 5α-reductase inhibitors, estrogen receptor modulators, estrogens, antiestrogens, gestagens, antigestagens, uterus-active substances, m-cholinoceptor antagonists, prostaglandins or prostaglandin derivatives and/or nicotine can be mentioned.

In a preferred embodiment, the composition according to the invention contains as active ingredient one or more androgens. As examples, MENT, MENTAc, eF-MENT, eF-MENTAc, testosterone, testosterone propionate, testosterone undecanoate, testosterone enanthate, mesterolone, nandrolone decanoate, clostebol acetate or metenolone acetate can be mentioned.

In a preferred embodiment, the composition according to the invention contains as active ingredient one or more antiandrogens, such as, e.g., cyproterone acetate, flutamide or bicalutamide.

In a preferred embodiment, the composition according to the invention contains as active ingredient one or more 5α-reductase inhibitors, such as, e.g., finasteride or 17α-estradiol.

In a preferred embodiment, the composition according to the invention contains as active ingredient one or more selective estrogen receptor modulators, such as, e.g., raloxifene.

In a preferred embodiment, the composition according to the invention contains as active ingredient one or more estrogens, such as, e.g., estradiol, estradiol valerate or estriol.

In a preferred embodiment, the composition according to the invention contains as active ingredient one or more conjugated estrogens, estrogen sulfamates or antiestrogens, such as, e.g., clomifene or taxol or partial antiestrogens, such as, e.g., raloxifene.

In a preferred embodiment, the composition according to the invention contains as active ingredient one or more gestagens, such as, e.g., progesterone, hydroxyprogesterone capronate, megestrol acetate, medroxyprogesterone acetate, chlormadinone acetate, cyproterone acetate, medrogestone, dydrogesterone, norethisterone, norethisterone acetate, norethisterone enanthate, levonorgestrel, gestodene, etonogestrel, dienogest, danazole, norgestimate, lynestrenol, desogestrel or drospirenone.

In a preferred embodiment, the composition according to the invention contains as active ingredient one or more antigestagens, such as, e.g., mifepristone or mesoprogestin.

In a preferred embodiment, the composition according to the invention contains as active ingredient one or more uterus-active substances, such as, e.g., oxytocin.

In a preferred embodiment, the composition according to the invention contains as active ingredient one or more m-cholinoceptor antagonists, such as, e.g., scopolamine.

In a preferred embodiment, the composition according to the invention contains as active ingredient one or more prostaglandins or prostaglandin derivatives, such as, e.g., alprostadil, gemeprost, dinoprostone, sulprostone, dinoprost, latanoprost or misoprostol.

In a preferred embodiment, the composition according to the invention contains nicotine as an active ingredient.

Also, a combination of two or more of the active ingredients above is preferred.

The necessary dosage of androgens, antiandrogens, 5α-reductase inhibitors, estrogen receptor modulators, estrogens, antiestrogens, gestagens, antigestagens, uterus-active substances, m-cholinoceptor antagonists, prostaglandins or prostaglandin derivatives and nicotine is known to one skilled in the art. In this connection, reference can be made to, for example, *Mutschler Arzneimittelwirkungen—Lehrbuch der Pharmakologie und Toxikologie [Pharmaceutical Agent Actions—Textbook of Pharmacology and Toxicology]*, 2001 and W. Forth et al., *Allgemeine und Spezielle Pharmakologie und Toxikologie [General and Special Pharmacology and Toxicology]*, B I Wissenschaftsverlag [Scientific Press] 1992, 6$^{th}$ Edition.

In a preferred embodiment, the composition according to the invention contains a combination of several active ingredients, selected from the group that consists of androgens and/or antiandrogens and/or 5α-reductase inhibitors and/or estrogen receptor modulators and/or estrogens and/or antiestrogens and/or gestagens and/or antigestagens and/or uterus-active substances and/or m-cholinoceptor antagonists and/or prostaglandins or prostaglandin derivatives and/or nicotine and/or compounds of general formula (III), (IV) and/or (V).

The composition according to the invention preferably contains additional contents as adjuvants.

In a preferred embodiment, the composition contains as adjuvants cyclomethicone and/or isopropyl myristate. In the hydrogel, cyclomethicone and isopropyl myristate ensure good spreading on and care of the skin. In a preferred embodiment, the composition contains glycerol as an adjuvant. Glycerol serves as a moisturizer for the composition and the skin.

In a preferred embodiment, the composition contains cyclomethicone, isopropyl myristate and glycerol as adjuvants. The proportion of water in the composition and the adjuvants produce in their combination a better compatibility of the composition. The concentration of nurturing adjuvants (cyclomethicone and isopropyl myristate) as well as the volatility of the cyclomethicone are important, since residues of the composition on the skin should be largely avoided—the latter could otherwise be contaminated by skin contact of the patient with another individual.

As additional adjuvants, polyethylene glycol and/or volatile silicone oils, such as, e.g., hexamethylcyclotrisiloxane, octamethylcyclotetrasiloxane and/or decamethylcyclopentasiloxane can be contained in the composition according to the invention. As adjuvants, in addition to water and $C_2$-$C_4$ alkyl alcohol, for example, the solvents benzyl alcohol, dimethylformamide or dimethyl sulfoxide can also be used. Preferred are also multivalent alcohols, such as ethylene glycol, propylene glycol, butylene glycol or hexylene glycol. To prevent the composition from drying out, in addition to or instead of glycerol, sorbitol, mannitol, polyethylene glycol and/or polypropylene glycol or a copolymer that consists of ethylene glycol and propylene glycol can be added. Glycerol has proven especially suitable. In addition, the pharmaceutical composition can contain, for example, dyes, perfumes, antioxidants, surfactants, bactericides, fungicides, complexing agents, cyclodextrins, electrolytes and/or viscosity aids. Such adjuvants are known to one skilled in the art. Relative to additional information, reference can be made to, for example, Fiedler, *Lexikon der Hiltsstoffe [Lexicon of Adjuvants]*, ECU Aulendorf 1996, 4$^{th}$ Edition and *Hunnius Studienausgabe [Hunnius Textbook Edition]*, de Gruyter 1993, 7$^{th}$ Edition.

The adjuvants improve the compatibility of the composition to the skin. The relative proportion of the adjuvants to the pharmaceutical composition is preferably 0.001-15.0% by weight, more preferably 0.01-10.0% by weight, even more preferably 0.5 to 5.0% by weight, especially 1.0 to 4.0% by weight. A proportion of 1.0-2.0% by weight of cyclomethicone and/or 0.3-0.8% by weight of isopropyl myristate and/or 0.5-1.5% by weight of glycerol is especially preferred.

The pharmaceutical composition according to the invention is a hydrogel. The water content of the hydrogel is preferably 5.0-90.0% by weight, more preferably 10.0-70.0% by weight, even more preferably 20.0-50.0% by weight, especially 25.0-40.0% by weight.

The relative ratio by weight of the $C_2$-$C_4$ alkyl alcohol to water is preferably 0. 1-10.0, more preferably 0.5-5.0, even more preferably 1.0-3.0, especially 1.8-2.2.

In a preferred embodiment of the invention, as a carboxylic acid diester, the pharmaceutical composition contains either propylene carbonate or ethylene carbonate, and, as a $C_2$-$C_4$ alkyl alcohol, the pharmaceutical composition contains ethanol. For this case, the pharmaceutical composition preferably contains 29.0-73.0% by weight of ethanol and 5.0-50.0% by weight of water, more preferably 34.0-68.0% by weight of ethanol and 10.0-45.0% by weight of water, even more preferably 39.0-63.0% by weight of ethanol and 15.0-40.0% by weight of water, especially preferably 44.0-58.0% by weight of ethanol and 20.0-35.0% by weight of water and especially 54.8-57.5% by weight of ethanol and 27.2-30.8% by weight of water.

The pH of the pharmaceutical composition according to the invention is preferably set at a value between 4.5 and 7.5, more preferably between 5.0 and 7.0, especially between 5.5 and 6.5. To this end, buffers such as, e.g., tris-(hydroxymethyl)-aminomethane, triethanolamine or bases, such as, e.g., diisopropylamine or potassium hydroxide, are suitable. Also, other suitable buffer substances and bases are known to one skilled in the art. Relative to further information, reference can be made to, for example, *Fiedler, Lexikon der Hilfsstoffe, ECU Aulendorf* 1996, 4$^{th}$ Edition and *Hunnius Studienausgabe, de Gruyter* 1993, 7$^{th}$ Edition.

The pharmaceutical composition according to the invention also contains a polymer matrix. This polymer matrix comprises at least one gel former and optionally one or more thickening agents, by which the rheological properties of the composition are improved. By the gel skeleton, patient compliance increases considerably, which is an essential advantage of the compositions according to the invention. A balance of properties is important, which is ensured by the composition according to the invention. A continuous use of the composition according to the invention is generally carried out by the patient, which does not cause any problems, however, especially because it is so easy to reapply the hydrogel to the skin.

Suitable gel skeleton formers are known in the prior art. According to the invention, as a gel skeleton former, the polymer matrix preferably comprises an acrylic polymer. The acrylic polymer can be a homopolymer or a copolymer.

The acrylic polymer is a homopolymer, thus the latter is preferably derived from an acrylic acid-$C_1$-$C_{30}$-alkyl ester or a methacrylic acid-$C_1$-$C_{30}$-alkyl ester.

The acrylic polymer is a copolymer, thus the latter is preferably derived from acrylic acid, methacrylic acid, acrylic acid-$C_1$-$C_{30}$-alkyl ester or methacrylic acid-$C_1$-$C_{30}$-alkyl ester in combination with one or more vinyl monomers. The vinyl monomer or monomers can either be acrylic acid, methacrylic acid, an acrylic acid-$C_1$-$C_{30}$-alkyl ester or a methacrylic acid-$C_1$-$C_{30}$-alkyl ester, but, for example, styrene, ethylene, propylene, vinyl chloride, vinylidene chloride, tetrafluoroethylene, vinyl acetate, vinyl ether or vinyl pyrrolidone can also be contained in the copolymer.

As acrylic polymers, especially homopolymers or copolymers, which are obtained by polymerization of acrylic acid, methacrylic acid, acrylic acid-$C_1$-$C_{30}$-alkyl ester and/or methacrylic acid-$C_1$-$C_{30}$-alkyl ester, are preferred.

The acrylic polymers that are contained in the composition according to the invention can be uncrosslinked or crosslinked. In a preferred embodiment, the composition according to the invention contains a crosslinked acrylic polymer.

The acrylic polymer is an uncrosslinked polymer, thus the weight-average molecular weight $M_w$ of the acrylic polymer preferably lies in the range of 50,000 to 2,500,000 gmol$^{-1}$, more preferably in the range of 100,000 to 2,000,000 gmol$^{-1}$, especially in the range of 500,000 to 1,500,000 gmol$^{-1}$.

As gel skeleton formers, the composition according to the invention especially preferably contains acrylic polymers, which are copolymers and are derived from a mixture that consists of acrylic acid and acrylic acid-$C_{10}$-$C_{30}$-alkyl esters. In an especially preferred embodiment, these copolymers are crosslinked, for example with allylpentaerythritol. Such crosslinked polymers are known in the prior art. For example, an acrylate-$C_{10}$-$C_{30}$-alkyl acrylate is commercially available under the designation Pemulen® TR1. This is an acrylate/C10-30 alkyl acrylate cross polymer. The general chemical structure of Pemulen® TR1 can be visualized in simplified terms as follows:

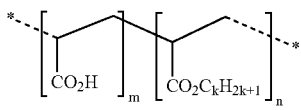

with k =10-30.

The proportion by weight of the gel skeleton former to the pharmaceutical composition is preferably 0.001-20.0% by weight, more preferably 0.005-10.0% by weight, even more preferably 0.01-5.0% by weight, especially 0.5-1.0% by weight.

In addition to the gel skeleton former, the polymer matrix of the composition according to the invention can contain additional polymers. The latter can act as thickening agents. According to the invention, as thickening agent, the composition preferably contains polyacrylic acid. Polyacrylic acid is marketed commercially, for example, under the designation Carbopol®. According to the invention, Carbopol® 980 is especially preferred.

The proportion by weight of polyacrylic acid to the pharmaceutical composition is preferably 0-5.0% by weight, more preferably 0.01-2.5% by weight, even more preferably 0.1-1.0% by weight, especially 0.3-0.5% by weight. In a preferred embodiment of the invention, the composition does not contain any polyacrylic acid.

In a preferred embodiment of the invention, in addition to the gel skeleton former, the polymer matrix contains as a thickening agent a cellulose derivative, but it is also possible that no cellulose derivative is present.

As preferred cellulose derivatives, methyl cellulose, ethyl cellulose, propyl cellulose, hydroxyethyl cellulose, hydroxypropyl cellulose, carboxymethyl cellulose, hydroxypropylmethyl cellulose, cellulose acetate butyrate, cellulose acetate propionate, hydroxypropylmethyl cellulose acetate succinate and methylhydroxypropyl cellulose phthalate or mixtures thereof can be mentioned. Ethyl cellulose, hydroxypropyl cellulose and hydroxypropylmethyl cellulose are especially preferred, especially ethyl cellulose and hydroxypropyl cellulose, whereby hydroxypropyl cellulose is most preferred.

Cellulose derivatives that are preferred according to the invention are compounds that have subunits of general formula (VI)

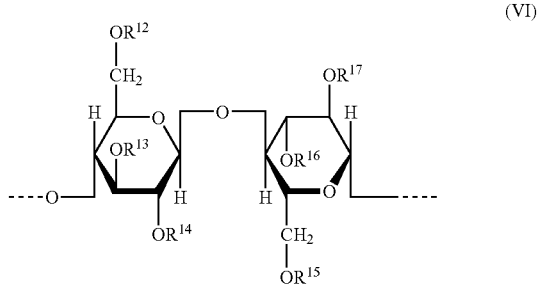

in which $R^{12}$, $R^{13}$, $R^{14}$, $R^{15}$, $R^{16}$ and $R^{17}$, in each case independently of one another, are hydrogen or a linear or branched $C_1$-$C_{61}$ alkyl radical, whose carbon chain can be interrupted up to 20 times with oxygen atoms and which optionally can be substituted with 1 or 2 hydroxyl groups, carboxyl groups or acyloxy groups, whereby the acyloxy groups optionally are derived from a $C_1$-$C_7$ carboxylic acid or $C_1$-$C_7$ dicarboxylic acid. $R^{12}$, $R^{13}$, $R^{14}$, $R^{15}$, $R^{16}$ and $R^{17}$ in each case independently of one another are preferably hydrogen or a linear or branched $C_1$-$C_{19}$ alkyl radical, whose carbon chain can be interrupted up to 6× with oxygen atoms and which optionally can be substituted with 1 or 2 hydroxyl groups.

The individual subunits of general formula (VI) can be substituted differently within the cellulose derivative. It is thus possible, for example, that in a first subunit, $R^{12}$, $R^{13}$, $R^{14}$, $R^{15}$ and $R^{16}$ are —$CH_2CH_3$, and $R^{17}$ is —H, while in another subunit, $R^{13}$, $R^{14}$, $R^{15}$, s $R^{16}$ and $R^{17}$ are —$CH_2CH_3$, and $R^{12}$ is —H.

The cellulose derivatives that are preferred according to the invention preferably exhibit a high degree of substitution relative to the hydroxyl groups of cellulose. The degree of substitution expressed as molar substitution (MS) is preferably from 2.0 to 6.0, more preferably 3.0 to 6.0, more preferably 3.0 to 5.0, especially 3.4 to 4.4.

Especially preferred substituents $R^{12}$, $R^{13}$, $R^{14}$, $R^{15}$, $R^{16}$ and $R^{17}$ are: —H, —$CH_3$, —$CH_2CH_3$, —$CH_2CH_2CH_3$, —CH(CH$_3$)$_2$, —CH$_2$CH$_2$CH$_2$CH$_3$, —CH$_2$CH$_2$OH, —CH$_2$CH(CH$_3$)OH, —[CH$_2$CH(CH$_3$)O]$_x$H, —CH$_2$CH (CH$_3$)OCH$_3$ and —[CH$_2$CH(CH$_3$)O]$_x$CH$_3$, in which x in each case can be a number from 2 to 20, preferably from 2 to 6, especially 2, 3 or 4.

According to the invention, the subunits of general formula (VI) are preferably subunits of hydroxypropyl cellulose, i.e., the radicals R$^{12}$, R$^{13}$, R$^{14}$, R$^{15}$, R$^{16}$ and R$^{17}$ are preferably, independently of one another, —H, —CH$_2$CH(CH$_3$)OH or —[CH$_2$CH(CH$_3$)O]$_x$H, in which in each case x can be a number from 2 to 20, preferably from 2 to 6. Hydroxypropyl cellulose can be obtained by reaction of alkali metal salts of cellulose with propylene oxide and subsequent neutralization of the alkoxy groups. If one of the hydroxyl groups of the cellulose in this reaction does not react with propylene oxide, R$^{12}$, R$^{13}$, R$^{14}$, R$^{15}$, R$^{16}$ or R$^{17}$ thus is —H. If one of the hydroxyl groups of the cellulose in this reaction reacts with one equivalent of propylene oxide, R$^{12}$, R$^{13}$, R$^{14}$, R$^{15}$, R$^{16}$ or R$^{17}$ thus is —CH$_2$CH(CH$_3$)OH. If one of the hydroxyl groups of the cellulose in this reaction reacts with one equivalent of propylene oxide and the alkoxide that is produced therefrom reacts with another equivalent of propylene oxide, R$^{12}$, R$^{13}$, R$^{14}$, R$^{15}$, R$^{16}$ or R$^{17}$ thus is —[CH$_2$CH(CH$_3$)O]$_x$H. Theoretically in this case, index x can be any number depending on how many equivalents oligomerize propylene oxide. Index x is preferably a number from 2 to 20, more preferably from 2 to 6, especially 2, 3 or 4.

R$^{12}$, R$^{13}$, R$^{14}$, R$^{15}$, R$^{16}$ and R$^{17}$, in each case independently of one another, especially preferably have one of the following meanings: —H, —CH$_2$CH(CH$_3$)OH, —[CH$_2$CH(CH$_3$) O]$_2$H or —[CH$_2$CH(CH$_3$)O]$_3$H.

According to the invention, a methyl cellulose, a hydroxypropylmethyl cellulose, an ethyl cellulose and especially a hydroxypropyl cellulose, in each case with a molar substitution (MS) of 3.0 to 6.0, more preferably 3.0 to 5.0, especially 3.4 to 4.4, is especially preferred.

Preferred cellulose derivatives are known to one skilled in the art. Ethyl cellulose, hydroxypropyl cellulose and hydroxypropylmethyl cellulose are commercially available, for example, under the designations Klucel®, Klucel® EXF (Aqualon®), Lucel® HF and Tylopur® MH 1000. Klucel® HF is especially preferred according to the invention. Relative to other information, reference can be made to, for example, *Fiedler, Lexikon der Hiltsstoffe, ECU Aulendorf* 1996, 4$^{th}$ *Edition* and *Hunnius Studienausgabe*, de Gruyter 1993, 7$^{th}$ *Edition*. Relative to other information on hydroxypropyl cellulose of the Klucel® type, reference can be made to Hercules, *Aqualon, Klucel®—Physical and Chemical Properties, Produkt-spezifikation [Product Specification]*, Hercules Incorporated 2001.

The weight-average molecular weight Mw of the cellulose derivative preferably lies in the range from 50,000 to 2,000, 000 gmol$^{-1}$, more preferably in the range from 300,000 to 1,500,000 gmol$^{-1}$, even more preferably in the range from 750,000 to 1,250,000 gmol$^{-1}$, especially in the range of 850, 000 to 1,150,000 gmol$^{-1}$.

The Brookfield viscosity of the cellulose derivative in water at 25° C. at a concentration of 1% is preferably 1,000 to 4,000 mPas, more preferably 1,275 to 3,500 mPas, especially 1,500 to 3,000 mPas. The measurement is performed with a Brookfield viscosimeter, Model LVF with 4 spindles and 4 speeds, with which the range of 0 to 100,000 mPas can be covered.

The proportion by weight of the cellulose derivative to the pharmaceutical composition is preferably 0-5.0% by weight, more preferably 0.01-2.5% by weight, even more preferably 0.1-1.5% by weight, and especially 0.3-1.0% by weight.

According to the invention, in addition to the acrylic polymer as a gel skeleton former, the polymer matrix alternatively comprises as a thickening agent either polyacrylic acid or a cellulose derivative. The combination of an acrylic polymer as a gel skeleton former with hydroxypropyl cellulose as a thickening agent is especially preferred.

The pharmaceutical compositions according to the invention can contain fatty acids with more than 12 carbon atoms or their esters or the fatty alcohols that are derived from these fatty acids or primary amines and/or C$_1$-C$_{18}$-alkyl ethers of mono-, di-, tri- or tetraethylene glycol, especially diethylene glycol monoethyl ether, and/or terpenes. These compounds are not necessary components of the pharmaceutical compositions according to the invention, however, and the pharmaceutical compositions according to the invention preferably contain none of these compounds.

In an especially preferred embodiment, the pharmaceutical composition contains the following components in the following proportions by weight:

TABLE 1

| Component | Proportion [%] by Weight] |
|---|---|
| eF-MENT | 0.01-5.0 |
| Acrylate/C10-30 alkyl acrylate Crosspolymer | 0.1-1.5 |
| Polyacrylic acid | 0-1.0 |
| Cellulose derivative | 0-2.0 |
| Propylene carbonate | 5.0-20.0 |
| 86% Glycerol | 0.01-5.0 |
| Cyclomethicone | 0.01-5.0 |
| Isopropyl myristate | 0.01-5.0 |
| Purified water | 20.0-50.0 |
| Ethanol | 30.0-60.0 |
| Tris-(hydroxymethyl)-aminomethane | at pH 5-7 |

The pharmaceutical compositions according to the invention are suitable as medications. The indication to be treated determines the active ingredient to be administered. Formulations according to the invention that contain steroids can be used, for example, to prevent and/or to treat different steroid deficiency symptoms. As exemplary applications, androgen replacement therapy, contraception, primary and secondary hypogonadism, testicular malfunction, hair loss, aging, loss and bone substance, muscular atrophy, erectile dysfunction, benign prostate hypertrophy, and prostate cancer can be mentioned. In particular, the compositions according to the invention that contain MENT, eF-MENT, MENTAc or eF-MENTAc are suitable for therapy or prevention of primary and secondary hypogonadism. Relative to pharmacology, biology and clinical applications of androgens, reference can be made to *Mutschler Arzneimittelwirkungen—Lehrbuch der Pharmakologie und Toxikologie*, 2001, S. Bhasin et al., *Pharmacology, Biology, and Clinical Applications of Androgens: Current Status and Future Prospects*, John Wiley & Sons, 1st Ed., 1996, Ch. Chawnshang, *Androgens and Androgen Receptor: Mechanisms, Functions, and Clinical Applications*, Kluwer Academic Publishers, 2002 and M. Carruthers, *Androgen Deficiency in the Aging Male*, CRC Press-Parthenon Publishers, 1$^{st}$ Ed., 2002.

The pharmaceutical compositions according to the invention are formulated for systemic administration of the active ingredient by local application on the skin. The compositions can either be applied by hand or a suitable adjuvant, such as, e.g., a spatula on the skin by spreading, but it is also possible to apply the compositions in the form of sprays on the skin.

The invention also relates to the use of a carboxylic acid diester for improving the transdermal permeation of an active ingredient in a pharmaceutical composition in the form of a hydrogel, whereby the composition in addition preferably comprises a $C_2$-$C_4$ alkyl alcohol, preferably ethanol, and a polymer matrix. Relative to the preferred components (i.e., relative to the active ingredients, the $C_2$-$C_4$ alkyl alcohols, the carboxylic acid diesters, the polymer matrix, the adjuvants, the buffer substances, etc.) and relative to the preferred quantitative ratios of these components in the pharmaceutical composition, reference can be made to the embodiments above. The invention thus relates to the use of a carboxylic acid diester, preferably a compound of general formula (I), more preferably a compound of general formula (II) and especially the use of propylene carbonate for improving the transdermal permeation of one or more active ingredients in a pharmaceutical composition in the form of a hydrogel, whereby the hydrogel preferably comprises a polymer matrix and a $C_2$-$C_4$ alkyl alcohol and preferably is defined as above.

According to the invention, it was also found, surprisingly enough, that a pharmaceutical composition in the form of a hydrogel, which comprises an acrylic polymer in combination with a cellulose derivative, no longer exhibits the problem that the gel skeleton is destroyed and the gel runs off if the gel is applied to skin that is wet from perspiration (sweat-resistant composition). To achieve this effect, the presence of a carboxylic acid diester in the formulation is not necessary.

According to the invention, such a pharmaceutical composition (sweat-resistant composition) comprises an acrylic polymer in combination with a cellulose derivative.

As a cellulose derivative, such a pharmaceutical composition (sweat-resistant composition) preferably contains a cellulose derivative, as was defined above, especially a compound that is selected from the group that consists of ethyl cellulose, hydroxypropyl cellulose and hydroxypropylmethyl cellulose. Ethyl cellulose and hydroxypropyl cellulose are especially preferred, whereby hydroxypropyl cellulose is more preferred. The molar substitution of the cellulose derivative is preferably 2 to 6, more preferably 3 to 6, especially 3 to 5, e.g., 3.4 to 4.4.

As an acrylic polymer, such a pharmaceutical composition (sweat-resistant composition) preferably contains an acrylic polymer, as it was defined above, especially a homopolymer or copolymer, which is derived from acrylic acid, methacrylic acid, acrylic acid-$C_1$-$C_{30}$-alkyl ester and/or methacrylic acid-$C_1$-$C_{30}$-alkyl ester. Especially preferred is a copolymer that is derived from a mixture that consists of acrylic acid and acrylic acid-$C_{10}$-$C_{30}$-alkyl esters. In an especially preferred embodiment, an acrylate/C10-30 alkyl acrylate is a crosspolymer.

The relative ratio by weight between the acrylic polymer and the cellulose derivative in the pharmaceutical composition (seat-resistant composition) is preferably 0.1-10.0, more preferably 0.2-5.0, even more preferably 0.5-2.0, and especially 0.75-1.75.

The total proportion of the acrylic polymer and the cellulose derivative to the pharmaceutical composition (sweat-resistant composition) is preferably 0.01-20.0% by weight, more preferably 0.1-10.0% by weight, even more preferably 0.3-5.0% by weight, and especially 1.0-2.0% by weight.

In a preferred embodiment, the pharmaceutical composition (sweat-resistant composition) contains 0.5-1.0% by weight of an acrylate/C10-30 alkyl acrylate crosspolymer in combination with 0.2-0.8% by weight of hydroxypropyl cellulose.

The pharmaceutical composition according to the invention (sweat-resistant composition) is preferably a hydrogel. The water content of the hydrogel is preferably 5.0-90.0% by weight, more preferably 10.0-70.0% by weight, even more preferably 20.0-50.0% by weight, and especially 25.0-40.0% by weight.

The pharmaceutical composition according to the invention (sweat-resistant composition) preferably contains a $C_2$-$C_4$ alkyl alcohol, whereby ethanol is especially preferred. For this case, the pharmaceutical composition (sweat-resistant composition) preferably contains 29.0-73.0% by weight of ethanol and 5.0-50.0% by weight of water, more preferably 34.0-68.0% by weight of ethanol, and 10.0-45.0% by weight of water, even more preferably 39.0-63.0% by weight of ethanol and 15.0-40.0% by weight of water, especially preferably 44.0-58.0% by weight of ethanol and 20.0-35.0% by weight of water, and especially 54.8-57.5% by weight of ethanol and 27.2-30.8% by weight of water.

In addition to the acrylic polymer and the cellulose derivative, the pharmaceutical composition (sweat-resistant composition) optionally contains at least one active ingredient and additional contents, such as, e.g., skin-care products, adjuvants, solvents, permeation enhancers, etc. The active ingredient, the optionally present additional contents and their preferred proportions, in percentage, in the composition are as defined above.

The pharmaceutical composition (sweat-resistant composition) in the form of a hydrogel thus preferably comprises an active ingredient and/or a carboxylic acid diester and/or a $C_2$-$C_4$ alkyl alcohol and/or a polymer matrix as defined above. Both the preferred proportions by weight, in percent, to the composition and relative ratios by weight of the individual components below one another and the preferred active ingredients, preferred carboxylic acid diesters and preferred $C_2$-$C_4$ alkyl alcohols are as defined above.

Instead of the carboxylic acid diester or supplementing the carboxylic acid diester, the pharmaceutical composition (sweat-resistant composition) can contain a permeation enhancer, which is selected from the group that consists of:

(i) aliphatic fatty acid esters that contain 10-30 carbon atoms and are optionally substituted with 1-2 hydroxyl groups, carboxyl groups or $C_1$-$C_4$ acyloxy groups;

(ii) aliphatic fatty acid alcohols that contain 10-30 carbon atoms and are optionally substituted with 1-2 hydroxyl groups, carboxyl groups or $C_1$-$C_4$ acyloxy groups; or (iii) a compound of general formula (VII)

$$HO\text{---}(CH_2CH_2\text{---}O)_n\text{---}R^{18} \quad\quad (VII)$$

in which $R^{18}$ is $C_1$-$C_{12}$-alkyl, $C_1$-$C_{12}$-alkenyl, $C_1$-$C_{12}$-alkanoyl or $C_1$-$C_{12}$-alkenoyl, and index n is a number from 1 to 10.

The pharmaceutical composition (sweat-resistant composition) preferably contains a compound of general formula (VII), in which $R^{18}$ is $C_1$-$C_4$-alkyl and index n is a number from 1 to 3.

Especially preferred compounds of general formula (VII) are: HO—$CH_2CH_2O$—$CH_3$, HO—$CH_2CH_2O$—$CH_2CH_3$, HO—$CH_2CH_2O$—$CH_2CH_2CH_3$, HO—$CH_2CH_2O$—$CH_2CH_2CH_2CH_3$, HO—$(CH_2CH_2O)_2$—$CH_3$, HO—$(CH_2CH_2O)_2$—$CH_2CH_3$, HO—$(CH_2CH_2O)_2$—$CH_2CH_2CH_3$, HO—$(CH_2CH_2O)_2$—$CH_2CH_2CH_2CH_3$, HO—$(CH_2CH_2O)_3$—$CH_3$, HO—$(CH_2CH_2O)_3$—$CH_2CH_3$, HO—$(CH_2CH_2O)_3$—$CH_2CH_2CH_3$, HO—$(CH_2CH_2O)_3$—$CH_2CH_2CH_2CH_3$, HO—$(CH_2CH_2O)_4$—$CH_3$, HO—$(CH_2CH_2O)_4$—$CH_2CH_3$, HO—$(CH_2CH_2O)_4$—$CH_2CH_2CH_3$ and HO—$(CH_2CH_2O)_4$—$CH_2CH_2CH_2CH_3$.

For the pharmaceutical composition (sweat-resistant composition), especially preferred is an embodiment that contains a compound of general formula (VII), in which $R^{18}$ is ethyl and index n=2, i.e., diethylene glycol monoethyl ether.

Figure 1:
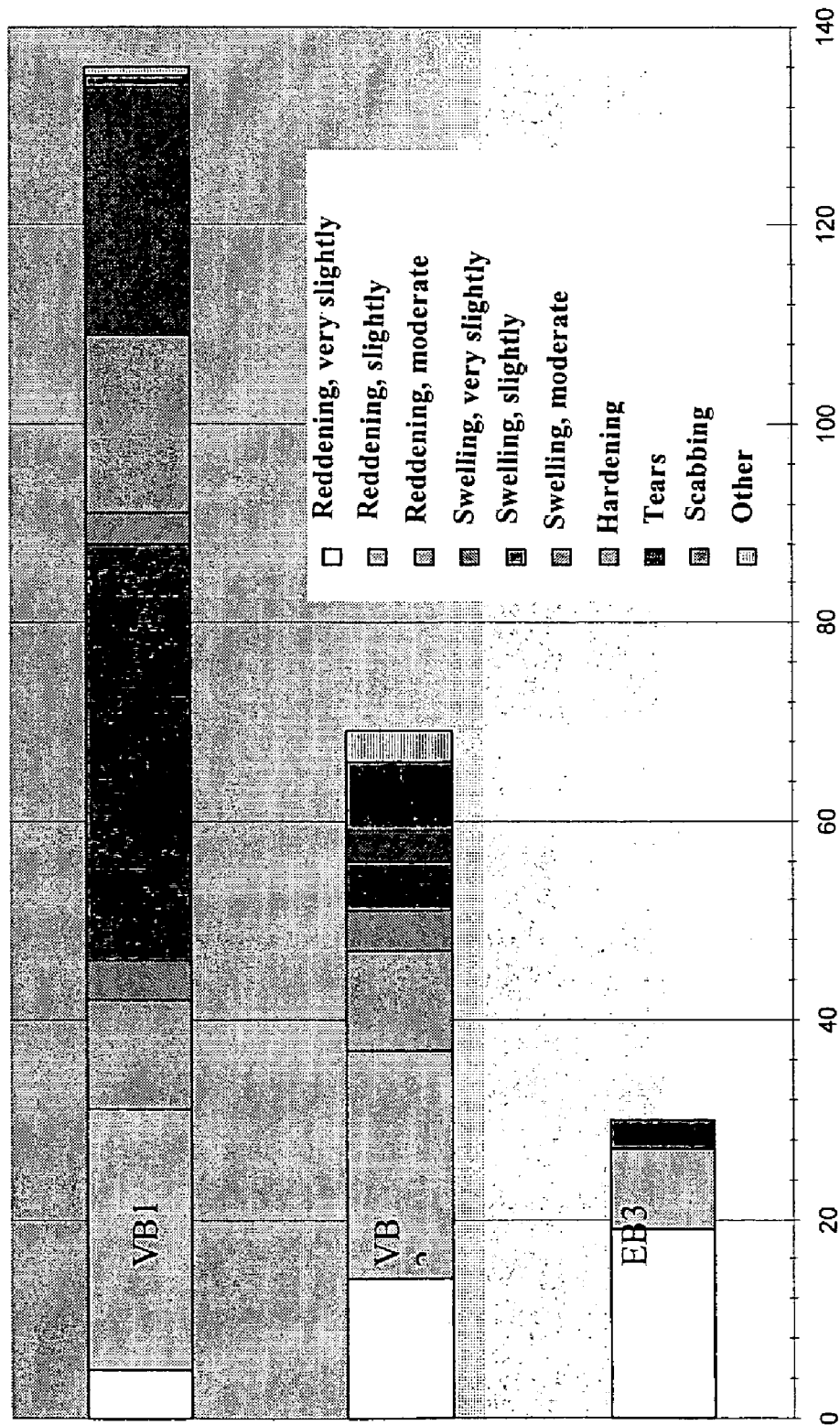
FIG. 1 depicts the comparison of formulas VB1, VB2 and EB3.

The following examples are used for further explanation of the invention.

EXAMPLE 1

Two pharmaceutical compositions according to the invention (Types A and B) were produced in the usual way. The components of the compositions are presented in Table 2:

TABLE 2

| Component | Amount [% by Weight] | |
|---|---|---|
| | Type A | Type B |
| Propylene carbonate | 10.0 | 10.0 |
| Ethanol | 55.0 | 55.0 |
| Purified water | about 30 | about 30 |
| eF-MENT | 0.8 | 0.8 |
| Acrylate/C10-30 alkyl acrylate Crosspolymer (Pemulen TR-1) | 0.8 | 0.8 |
| Polyacrylic acid | — | 0.4 |
| Hydroxypropyl cellulose (Klucel HF) | 0.35 | — |
| 86% Glycerol | 1.0 | 1.0 |
| Cyclomethicone | 1.5 | 1.5 |
| Isopropyl myristate | 0.5 | 0.5 |
| Tris-(hydroxymethyl)aminomethane | at pH 5.8 | at pH 5.8 |

EXAMPLE 2

Best Mode

A pharmaceutical composition (sweat-resistant composition, type C) in the form of a hydrogel, which comprises an acrylic polymer in combination with a cellulose derivative, was produced without an active ingredient. The components of the compositions are presented in Table 3:

TABLE 3

| Component | Amount [% by Weight] of Type C |
|---|---|
| Propylene carbonate | 10.0 |
| Ethanol | 55.0 |
| Purified water | about 30 |
| Acrylate/C10-30 alkyl acrylate Crosspolymer (Pemulen TR-1) | 0.8 |
| Hydroxypropyl cellulose (Klucel HF) | 0.35 |
| 86% Glycerol | 1.0 |
| Cyclomethicone | 1.5 |
| Isopropyl myristate | 0.5 |
| Tris-(hydroxymethyl)aminomethane (Tromethamine) | at pH 5.8 |

The following production process was performed:

Pemulen TR-1 and HPC (Klucel HF) were steeped in 96% ethanol. Propylene carbonate was added and mixed while being stirred. Then, isopropyl myristate was added, and it was mixed again. The gel former and the swelling substance began to swell in the solvent mixture. The entire mixture was introduced via a hopper in a mixer/homogenizer system (Becomix RW 2.5) (drawn into the Becomix RW 2.5) and stirred briefly at 20 rpm. Then, it was homogenized for 1 minute at 2000-3500 rpm (e.g., with a rotor-stator homogenizer). A homogeneous, clear gel with no agglomerates that was still not completely steeped was obtained. 86% glycerol and the entire amount of the purified water were added as a streak-free mixture in several partial steps (drawn in), and the gel again swelled considerably. It was stirred (about 5 minutes) until a significant clearing-up of the gel was visible. With each addition of water/glycerol, the gel skeleton was better formed and also became increasingly more clear at the same time. The rpm was 50. Then, cyclomethicone was added to the mixture while being stirred. A uniform distribution of the water/glycerol mixture as well as the cyclomethicone is thus ensured, and it was homogenized at the end of the addition for 1 more minute at 4000 rpm. Then, while being stirred at 50 rpm in 3 partial sections, a 10% aqueous tromethamine solution was added for neutralization. The gel in this case became considerably clearer, and the gel structure built up further. At the end of the addition, it was homogenized again for 2 minutes at 2700 rpm.

EXAMPLE 3

In a series of tests, 3 different pharmaceutical compositions in the form of hydrogels were examined with respect to their skin compatibility. The formulations were as follows:

Comparison Formulation 1 (VB1) (Example According to the Disclosure of EP-A 817 621):
70.2% ethanol, 20% ethylhexyl ethylhexanoate, 1% cetearyl octanoate; 1.5% hydroxypropyl cellulose; 3.6% water Comparison Formulation 2 (VB2); Androgel (Market Product):
68.9% ethanol; isopropyl myristate, polyacrylic acid, water, NaOH Formulation 3 According to the Invention (EB3), Produced According to the Process of Example 2:

45% ethanol, 10% propylene carbonate, 2.0% PEG 400, 0.6% acrylic polymer, 4.0% glycerol, 37.25% water, diisopropylamine q.s.

The local compatibility in rabbits after once-daily dermal application of 0.25 g per application site over 2 weeks (a total of 14 applications) on the intact skin was examined. The study was carried out according to the EMEA Guidelines (CPMP/SWP/2145/00). The study was carried out on 6 male animals (white New Zealand/conv.) As a negative control, tap water was used; as a positive control, testogel/androgel was used. The exposure time was 4 hours. Treatment residues were removed with lukewarm water. The reading and evaluation of the reaction was carried out in each case at the end of the exposure time before the removal of the substance residue. The animals were sacrificed and dissected on the day after the last treatment (day 15). The sampling as well as the histological working-up were carried out according to the information of SOP TX ME No. 382.4.

The results are shown in FIG. 1, whereby the X-axis indicates the number of indications, and the formulations are indicated on the Y-axis.

As the comparison tests indicate, the composition according to the invention is superior to the commonly used compositions of the prior art. As comparison formulations 1 and 2 (VB1 and VB2) indicate, gels that have a high ethanol content show significant side effects. In this case, it is clear that the side effects are not caused exclusively by the ethanol but apparently are also dependent on the type of permeation enhancer that is used. At an ethanol content of 70% by weight, the marketed product (androgel) shows considerably fewer side effects than comparison formulation 1 (VB1), in which ethylhexyl ethylhexanoate served as a permeation enhancer (cf. product according to EP-A 817 621).

EXAMPLE 4

Rheological characterization of the electrolyte tolerance of gel systems based on polyacrylic acid (e.g., carbopol) versus gel systems based on a combination of hydroxypropyl cellulose and Pemulen TR-1 (sweat-resistant composition).

The test set-up simulates the "sweat-resistance" of the described gel systems on the skin. To this end, selected electrolyte preparations are added to the composition, and the rheological parameters are determined. The electrolyte tolerance is characterized by comparison of the untreated sample with the electrolyte-loaded sample.

The preparations were mixed with 0.01% NaCl in crystalline form, and the salt was added while being stirred moderately. Then, the rheological measurement was carried out immediately. The measuring apparatus consisted of a rotary viscosimeter RC 20 of the Europhysics Company with a Peltier thermostat. The measuring temperature was 25° C., and the preset value of the shear stress (τ) was 150 Pascal. The C50-1 measuring cone was used.

1. Androgel based on polyacrylic acid (Carbopol) (market product androgel)
2. Vehicle according to the invention based on hydroxypropyl cellulose (Klucel HF)/Pemulen TR-1, hydrogel according to Example 2

The yield points of the androgel dropped because of the electrolyte load to about 17% of the starting value. The yield points of the variant according to the invention based on hydroxypropyl cellulose/Pemulen TR-1 were reduced to only about 89% of the starting value, however.

TABLE 4

| Feedstock | Yield Points (Pa) | Residual Yield Points (in Percent of the Starting Value) |
|---|---|---|
| Androgel without Electrolyte | 15.3 | 16.7 |
| Androgel with 0.01% NaCl | 2.5 | |
| Vehicle According to he Invention without Electrolyte | 22.9 | 89.5 |
| Vehicle According to the Invention with 0.01% NaCl | 20.3 | |

For the system based on hydroxypropyl cellulose/Pemulen TR-1, the results show a considerably higher electrolyte tolerance. This behavior correlates with the real-life application experience. The preparation according to the invention can be applied without running off and dripping off from the skin. However, it results in the market product androgel running off and dripping off, which is caused by the strong reduction in yield points.

EXAMPLE 5

The permeation behavior relative to active ingredient eF-MENT of a composition according to the invention, which contained 55% by weight of ethanol and 10% by weight of propylene carbonate, and had been produced above according to Example 2, was compared to the permeation behavior from a composition that corresponded approximately to the composition of the market product androgel.

The experiment was performed with the aid of a Franz diffusion cell (cf. T. J. Franz, *Invest. Dermatol.* 1975, 64, 191). This model consists of a diffusion cell, which can be subdivided into a donor compartment and an acceptor compartment. In this system, the skin acts as a barrier between these compartments. In this case, the skin is introduced between the compartments, such that the dermal side is flushed by the solution of the acceptor compartment. The acceptor compartment of the diffusion cell is connected to an HPLC unit, by which an automatic analysis of aliquots of the solution is possible.

The actual composition of the tested hydrogel according to the invention is presented in Table 5:

TABLE 5

| Component | [% by Weight] |
|---|---|
| Propylene carbonate | 10.0 |
| Ethanol | 55.0 |
| Purified water | ~29.0 |
| eF-MENT | 0.8 |
| Acrylate/C10-30 alkyl acrylate Crosspolymer (Pemulen TR-1) | 0.8 |
| Methyl cellulose (Tylopur MH 1000, obtainable from the Clariant Company) | 0.5 |
| 86% Glycerol | 1.0 |
| Cyclomethicone | 1.5 |
| Isopropyl myristate | 0.5 |
| Tris-(hydroxymethyl)aminomethane | at pH 5.8 |

The skin of hairless mice (HsdCpb NMRI-nu/nu, Harlan Bioservice, Walsrode) was examined.

The solution in the acceptor compartment had the following composition:

Potassium chloride 0.4 g

Potassium dihydrogen phosphate 0.06 g

Sodium chloride 7.27 g

Sodium hydrogen phosphate dihydrate 0.06 g

HEPES 5.96 g

Gentamicin sulfate 0.05 g

γ-Cyclodextrin 5.0 g

Aqua purificata to 1000 g

In the experiments, aliquots of 250 µl of the sample were applied on the surface of the epidermal side of the skin (45 cm$^2$) with the aid of a syringe. With the fingertips, which were protected by gloves, the samples were rubbed lightly on the skin surface. Five minutes after the gel was applied, a portion of the skin was introduced into the diffusion cell. The acceptor solution of the Franz cell was continuously homogenized. The available permeation surface area was 1.5 cm$^2$. After specified time intervals (3, 6, 9, 12, 15 and 18 hours), aliquots of the acceptor solution were removed, injected into the HPLC unit and automatically analyzed. The content of eF-MENT in the samples was quantified with the aid of standard solutions, whereby the standard solutions were measured in parallel and under the same HPLC conditions.

HPLC:
Column: Vertex with precolumn, Nucleosil—100 C18, 5 μm, 125×3 mm
Mobile Phase: Acetonitrile/water (39/61)
Flow rate: 0.700 ml/min
Temperature: 40° C.
Injection volume: 200 μl
Detecion wavelength: 244 nm
Retention time: eF-MENT 4.8 minutes.

Figure 2:
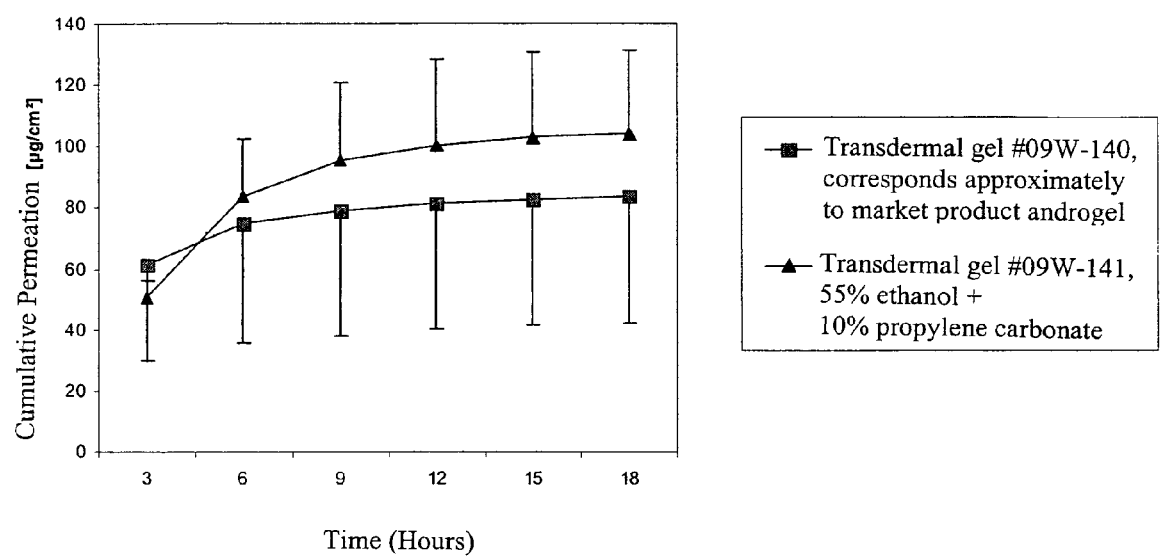
FIG. 2 depicts the comparison of transdermal gel #09W-140 vs. transdermal gel #09W-141.

The results of the studies are illustrated in FIG. 2 (transdermal gel #09W-140 is used as a comparison example; transdermal gel #09W-141 is the example according to the invention).

The experiments confirm that the composition according to the invention (#09W-141), while having improved compatibility and improved application properties, exhibits very good permeation efficiency with respect to the active ingredient that is to be administered transdermally.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosure[s] of all applications, patents and publications, cited herein and of corresponding European application No. 03008856.1, filed Apr. 28, 2003, and U.S. Provisional Application Ser. No. 60/465,808, filed Apr. 28, 2003 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A composition in the form of a hydrogel comprising 0.01-5.0% by weight of 7α-methyl-11β-fluoro-19-nortestosterone (eF-MENT), 0.1-1.5% by weight of acrylate/$C_{10-30}$ alkyl acrylate crosspolymer, 0-1.0% by weight of polyacrylic acid, 0.1-1.5% by weight of a cellulose derivative, 5.0-20.0% by weight of propylene carbonate, 0.01-5.0% by weight of glycerol, 0.01-5.0% by weight of cyclomethicone, 0.01-5.0% by weight of isopropyl myristate, 20.0-50.0% by weight of purified water, 30.0-60.0% by weight of ethanol and tris-(hydroxymethyl)-aminomethane at pH 5-7.

2. A method for treating steroid deficiency symptoms comprising administering a hydrogel as defined in claim 1.

3. A composition in the form of a hydrogel according to claim 1 comprising:
7.5-12.5% by weight of propylene carbonate,
40.0-60.0% by weight of ethanol, and
25.0-40.0% by weight of purified water.

4. A hydrogel according to claim 1, wherein the amount of water is from 25-40% by weight.

5. A hydrogel according to claim 1, wherein said cellulose derivative is a hydroxypropyl cellulose.

* * * * *